US00PP27809P3

(12) United States Plant Patent
Trees

(10) Patent No.: US PP27,809 P3
(45) Date of Patent: Mar. 21, 2017

(54) ***SCABIOSA* PLANT NAMED 'BALFLUTTROPI'**

(50) Latin Name: *Scabiosa columbaria*
Varietal Denomination: Balfluttropi

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 81 days.

(21) Appl. No.: 14/756,103

(22) Filed: Jul. 30, 2015

(65) Prior Publication Data
US 2017/0034982 P1 Feb. 2, 2017

(51) Int. Cl.
*A01H 5/02* (2006.01)

(52) U.S. Cl.
USPC ..... Plt./478

(58) Field of Classification Search
USPC ..... Plt./478
See application file for complete search history.

*Primary Examiner* — Anne Grunberg
(74) *Attorney, Agent, or Firm* — Audrey Charles

(57) ABSTRACT

A new and distinct cultivar of *Scabiosa* plant named 'Balfluttropi', characterized by its medium purple-colored flowers, dark green-colored foliage, and moderately vigorous, compact-mounded growth habit, is disclosed.

1 Drawing Sheet

Latin name of genus and species of plant claimed: *Scabiosa columbaria.*

Variety denomination: 'Balfluttropi'.

BACKGROUND OF THE INVENTION

The present invention relates to a new and distinct cultivar of *Scabiosa* plant botanically known as *Scabiosa columbaria* and hereinafter referred to by the cultivar name 'Balfluttropi'.

The new cultivar originated in a controlled breeding program in Guadalupe, Calif. during September 2010. The objective of the breeding program was the development of *Scabiosa* cultivars that have large inflorescences with rich flower colors and a compact growth habit.

The new *Scabiosa* cultivar is the result of open-pollination. The female (seed) parent of the new cultivar is the proprietary *Scabiosa columbaria* breeding selection coded SCB-191, not patented, characterized by its light lavender-blue colored flowers, dark green-colored foliage, and moderately vigorous, semi-upright growth habit. The male (pollen) parent of the new cultivar is unknown. The new cultivar was discovered and selected as a single flowering plant within the progeny of the above stated open-pollination during September 2011 in a controlled environment in Guadalupe, Calif.

Asexual reproduction of the new cultivar by terminal stem cuttings since September 2011 in Guadalupe, Calif., and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfluttropi' as a new and distinct cultivar of *Scabiosa* plant:

1. Medium purple-colored flowers;
2. Dark green-colored foliage; and
3. Moderately vigorous, compact-mounded growth habit.

Of the many commercially available *Scabiosa* cultivars, the most similar in comparison to the new cultivar is 'Pink Mist', U.S. Plant Pat. No. 8,957. However, in side-by-side comparison, plants of the new cultivar differ from plants of 'Pink Mist' in at least the following characteristics:

1. Plants of the new cultivar have shorter peduncles under warmer growth conditions than plants of 'Pink Mist'; and
2. Plants of the new cultivar have a flower color that is darker than plants of 'Pink Mist'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balfluttropi'. The plants were grown in 1 gallon containers for approximately 8 weeks in a greenhouse and 9 weeks outdoors in Elburn, Ill.

DETAILED BOTANICAL DESCRIPTION

Figure 1:
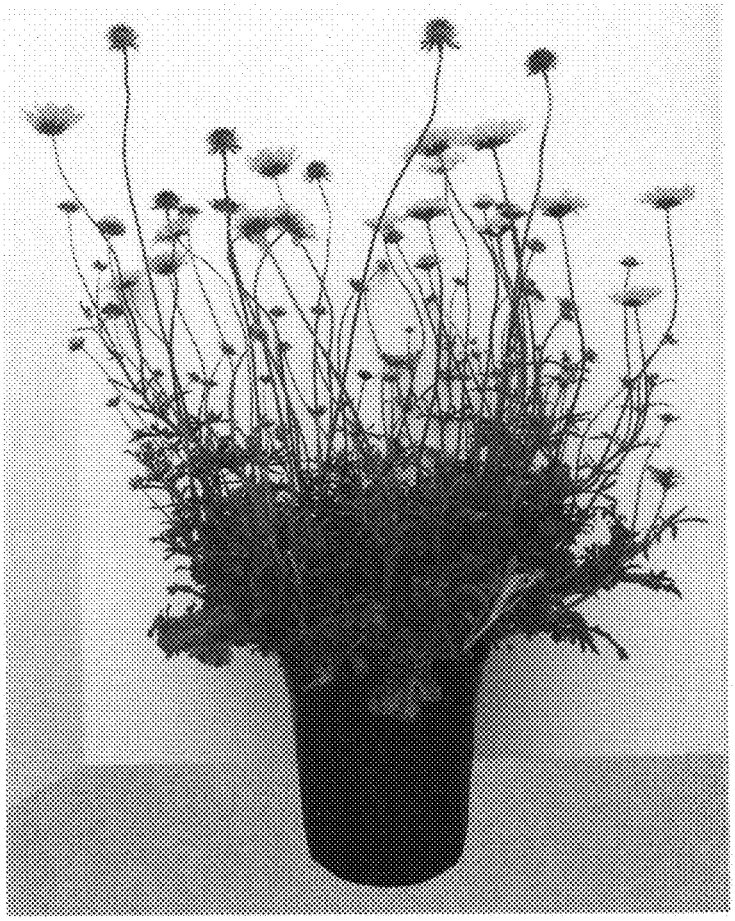
FIG. 1 illustrates a side view of the overall growth and flowering habit of 'Balfluttropi'.
Figure 2:
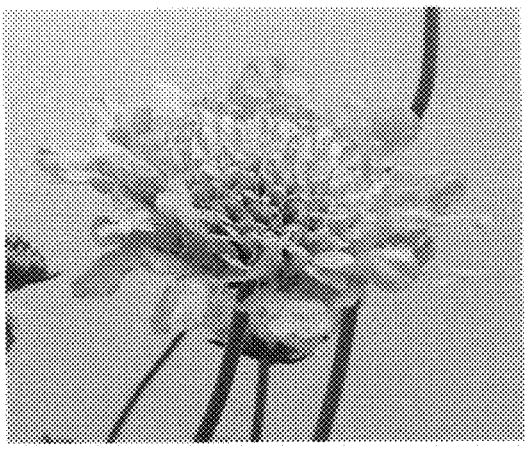
FIG. 2 illustrates a close-up view of an individual inflorescence of 'Balfluttropi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2015 under natural light conditions in West Chicago, Ill.

The following descriptions and measurements describe plants produced from cuttings from stock plants and grown under conditions comparable to those used in commercial practice. The plants were grown in 1 gallon containers for approximately 8 weeks in a greenhouse and 9 weeks outdoors in Elburn, Ill. Greenhouse temperatures were maintained at approximately 60° F. to 68° F. (15.5° C. to 20° C.) during the day and approximately 55° F. to 60° F. (13° C. to 15.5° C.) during the night. No supplemental lighting was provided. Measurements and numerical values represent averages of typical plants.

Botanical classification: *Scabiosa columbaria* cultivar Balfluttropi.

Parentage:

*Female parent*.—Proprietary *Scabiosa columbaria* breeding selection coded SCB-191, not patented.

*Male parent*.—Unknown.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fibrous, fine to medium, creamy white to light brown in color.

*Rooting habit*.—Freely branching, medium density.

Plant description:

*Commercial crop time*.—Approximately 8 to 10 weeks from a rooted cutting to finish in a 10 cm pot.

*Growth habit and general appearance*.—Moderately vigorous, compact-mounded.

*Size*.—Height from soil level to top of plant plane: Approximately 63.0 cm. Width: Approximately 46.0 cm.

*Branching habit*.—Basal rosette, freely branching, pinching enhances basal branching. Quantity of main stems per plant: Approximately 9, with each main branch having 4 to 6 lateral branches.

*Main stems*.—Strength: Strong. Length to base of peduncle: Approximately 16.0 cm. Diameter: Approximately 6.0 mm. Length of central internode: Approximately 5.5 mm. Texture: Densely pubescent with appressed hairs. Color of young and mature stems: Close to 138A, appears lighter due to pubescence.

Foliage description:

*General description*.—Quantity of leaves per main branch: Approximately 12. Fragrance: None detected. Form: Simple. Arrangement: Opposite.

*Leaves*.—Aspect: Acute angle to stem, tips turning downward with age. Shape: Overall narrowly obovate. Margin: Pinnatisect, less dissected earlier in season and as a young plant. Apex: Acuminate. Base: Attenuate, sessile. Venation pattern: Pinnate. Length of mature leaf: Approximately 13.0 cm. Width of mature leaf: Approximately 5.0 cm. Texture of upper surface: Sparsely pubescent with appressed hairs. Texture of lower surface: Moderately pubescent, venation densely pubescent with appressed hairs. Color of upper surface of young and mature foliage: 137A with venation indistinguishable from leaf lamina except for midvein of 145C. Color of lower surface of young and mature foliage: 137B with venation indistinguishable from leaf lamina except for midvein of 145A.

Flowering description:

*Flowering habit*.—'Balfluttropi' is freely flowering under outdoor growing conditions with substantially continuous blooming from late spring through late summer.

*Lastingness of individual inflorescence on the plant*.—Approximately 8 to 10 days.

Inflorescence description:

*General description*.—Type: Involucrate heads. Corolla not persistent, bristled calyx persistent. Shape: Dome. Aspect: Facing upward to slightly outward. Arrangement: Terminal involucrate heads displayed above the foliar plane on long peduncles. Fragrance: None detected. Quantity per plant: Approximately 17. Diameter: Approximately 5.3 cm. Inner cushion diameter: Approximately 2.5 cm. Depth: Approximately 1.8 cm.

*Peduncle*.—Strength: Strong. Aspect: Erect to slightly wiry. Length: Approximately 29.5 cm. Diameter: Approximately 3.0 mm. Texture: Densely pubescent with appressed hairs. Color: Close to 138A, appears lighter due to pubescence.

*Inflorescence bud*.—Rate of opening: Generally takes 2 to 4 days for bud to progress from first color to fully open flower.

*Bud just before opening*.—Shape: Obovate. Length: Approximately 6.0 mm. Diameter: Approximately 2.0 mm. Color: 145D with 77B at apex.

*Outer florets*.—Quantity per inflorescence: Approximately 16. Arrangement: In two whorls. Shape: Funnel, 5 lobes, 3 broad upper lobes with the central lobe being the largest, and 2 small lower lobes. Lobes are fused at the base forming a tube. Length: Approximately 2.4 cm. Width: Approximately 1.4 cm. Upper lobes: Shape: Narrowly obovoid to oblong. Margin: Scalloped. Apex: Erose to rounded. Length of central lobe from throat: Approximately 1.4 cm. Width of central lobe: Approximately 7.0 mm. Length of lateral lobes from throat: Approximately 8.0 mm. Width of lateral lobes: Approximately 6.0 mm. Texture of upper surface: Glabrous. Texture of lower surface: Central lobe and base of lateral lobes densely pubescent. Color of upper surface when fully open: 77C fading to 76B with age. Color of lower surface when fully open: 77D with margins of 76B and NN155D at base. Lower lobes: Shape: Obovate. Margin: Entire, slightly wavy. Apex: Scalloped. Length from throat: Approximately 4.0 mm. Width: Approximately 4.0 mm. Texture of upper surface: Glabrous. Texture of lower surface: Base densely pubescent. Color of upper surface when fully open: 77C fading to 76B with age. Color of lower surface when fully open: 77D with margins of 76B and NN155D at base. Tube: Length: Approximately 1.0 cm. Diameter at base: Approximately 1.0 mm. Diameter at throat: Approximately 2.0 mm. Texture of inner surface: Sparsely pubescent. Texture of outer surface: Densely pubescent. Color of inner and outer surfaces: NN155D.

*Inner florets*.—Quantity per inflorescence: Approximately 53. Arrangement: In multiple whorls. Shape: Funnel, 5 lobes, 3 broad upper lobes with the central lobe being the largest, and 2 small lower lobes. Lobes are fused at the base forming a tube. Length: Approximately 1.5 cm. Width: Approximately 4.0 mm. Upper lobes: Shape: Oblong. Margin: Entire, slightly wavy. Apex: Rounded. Length of central lobe from throat: Approximately 4.0 mm. Width of central lobe: Approximately 2.0 mm. Length of lateral lobes from throat: Approximately 2.0 mm. Width of lateral lobes: Approximately 2.0 mm. Texture of upper surface: Glabrous. Texture of lower surface: Central lobe and lower half of lateral lobes densely pubescent. Color of upper surface when fully open: NN155D blushed with 77C. Color of lower surface when fully open: NN155D central lobe blushed with 77C. Lower lobes: Shape: Orbicular. Margin: Entire, slightly wavy. Apex: Rounded. Length from throat: Approximately 1.5 mm. Width: Approximately 1.5 mm. Texture of upper surface: Glabrous. Texture of lower surface: Lower half densely pubescent. Color of upper surface when fully open: NN155D blushed with 77C. Color of lower surface when fully open: NN155D. Tube: Length: Approximately 8.0 mm. Diameter at base: Approximately 1.0 mm. Diameter at throat: Approximately 2.0 mm. Texture of inner surface: Sparsely pubescent. Texture of outer surface: Densely pubescent. Color of inner and outer surfaces: NN155D.

*Calyx*.—Arrangement: 2 whorls. Outer whorl: 5 fused sepals. Shape: Cup-like. Height: Approximately 2.0 mm. Width: Approximately 2.0 mm. Apex: Scalloped. Texture of inner surface: Glabrous. Texture of outer surface: Densely pubescent. Color of inner and outer surfaces: NN155D, translucent with base of 137A. Inner whorl: 5 pappus-like setae attached at base. Length: Approximately 7.0 mm. Color: 187A with base of 144A.

*Floral bracts*.—Quantity: One per floret. Shape: Obovate. Margin: Entire. Apex: Acute. Base: Attenuate. Length: Approximately 4.0 mm. Width: Approximately 1.0 mm. Texture of inner surface: Glabrous. Texture of outer surface: Densely pubescent. Color of inner and outer surfaces: 137A, outer surface appears lighter due to pubescence.

*Involucral bracts*.—Quantity per inflorescence: Approximately 13. Arrangement: In a single whorl. Shape: Linear to lanceolate. Margin: Entire. Apex: Acute. Base: Truncate. Length: Approximately 1.1 cm. Width: Approximately 2.0 mm. Texture of inner surface: Moderately pubescent. Texture of outer surface: Densely pubescent. Color of inner and outer surfaces: 137A, outer surface appears lighter due to pubescence.

*Receptacle*.—Shape: Conical. Height: Approximately 3.0 mm. Diameter: Approximately 3.0 mm. Color: Closest to N144A.

*Reproductive organs*.—Androecium and gynoecium: Present on both inner and outer florets. Stamen quantity: 4 per floret, base of filaments adnate to corolla. Stamen length: Approximately 7.0 mm. Filament length of free portion: Typically 1.0 mm. Filament color: NN155D. Anther shape: Oblong. Anther length: Approximately 2.0 mm. Anther color: 161B. Pollen amount: Not observed. Pistil quantity: 1 per floret. Pistil length: Approximately 1.5 cm. Stigma shape: Oblate. Stigma length: Less than 1 mm. Stigma color: Close to NN155D. Style length: Approximately 1.4 cm. Style color: NN155D with an overlay of 77B on upper third. Ovary length: Approximately 1.0 mm. Ovary color: NN155D.

Seed and fruit production: Neither seed nor fruit production has been observed.

Disease and pest resistance: Resistance to pathogens and pests common to *Scabiosa* has not been observed.

What is claimed is:

1. A new and distinct cultivar of *Scabiosa* plant named 'Balfluttropi', substantially as herein illustrated and described.

* * * * *